US00PP21632P2

(12) United States Plant Patent
Keiser

(10) Patent No.: US PP21,632 P2
(45) Date of Patent: Jan. 18, 2011

(54) ***ABELIA* PLANT NAMED 'KEISER'**
(50) Latin Name: *Abelia Chinensis*
Varietal Denomination: Keiser

(75) Inventor: Susan Keiser, Ossining, NY (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 12/587,680

(22) Filed: Oct. 10, 2009

(51) Int. Cl.
*A01H 5/00* (2006.01)

(52) U.S. Cl. ..... Plt./226
(58) Field of Classification Search ..... Plt./226
See application file for complete search history.

*Primary Examiner*—June Hwu
(74) *Attorney, Agent, or Firm*—C. A. Whealy

(57) ABSTRACT

A new and distinct cultivar of *Abelia* plant named 'Keiser', characterized by its upright and outwardly spreading plant habit; freely branching habit; dense and bushy growth habit; burgundy-colored developing stems; burgundy-tinted leaves; numerous white-colored flowers; and fragrant flowers.

2 Drawing Sheets

Botanical designation: *Abelia chinensis.*
Cultivar denomination: 'KEISER'.

BACKGROUND OF THE INVENTION

The present invention relates to a new and distinct cultivar of *Abelia* plant, botanically known as *Abelia chinensis* and hereinafter referred to by the name 'Keiser'.

The new *Abelia* plant originated from a cross-pollination in 1999 of two unnamed selections of *Abelia chinensis,* not patented. The new *Abelia* plant was discovered and selected by the Inventor in 2002 as a flowering plant within the progeny of the stated cross-pollination in a controlled environment in Ossining, N.Y.

Asexual reproduction of the new *Abelia* plant by softwood cuttings in a controlled greenhouse environment in Grand Haven, Mich. since 2006 has shown that the unique features of this new *Abelia* plant are stable and reproduced true to type in successive generations of asexual reproduction.

SUMMARY OF THE INVENTION

Plants of the new *Abelia* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Keiser'. These characteristics in combination distinguish 'Keiser' as a new and distinct cultivar of *Abelia:*

1. Upright and outwardly spreading plant habit.
2. Freely branching habit; dense and bushy growth habit.
3. Burgundy-colored developing stems.
4. Burgundy-tinted leaves.
5. Numerous white-colored flowers.
6. Fragrant flowers.

Plants of the new *Abelia* can be compared to plants of the parent selections. Plants of the new *Abelia* differ from plants of the parent selections in the following characteristics:

1. Plants of the new *Abelia* are more upright than plants of the parent selections.

2. Leaves of plants of the new *Abelia* are burgundy-tinted whereas leaves of plants of the parent selections are green in color.
3. Plants of the new *Abelia* have larger flowers than plants of the parent selections.
4. Flowers of plants of the new *Abelia* are more fragrant than flowers of plants of the parent selections.

Plants of the new *Abelia* can be compared to plants of the *Abelia chinensis* 'Edward Goucher', not patented. In side-by-side comparisons conducted in Grand Haven, Mich., plants of the new *Abelia* differed from plants of 'Edward Goucher' in the following characteristics:

1. Flowers of plants of the new *Abelia* were white in color whereas flowers of plants of 'Edward Goucher' were red purple in color.
2. Plants of the new *Abelia* had larger and more fragrant flowers than plants of 'Edward Goucher'.

BRIEF DESCRIPTION OF THE PHOTOGRAPHS

The accompanying colored photographs illustrate the overall appearance of the new *Abelia* plant, showing the colors as true as it is reasonably possible to obtain in colored reproductions of this type. Colors in the photographs may differ slightly from the color values cited in the detailed botanical description which accurately describe the colors of the new *Abelia* plant.

The photograph on the first sheet is a top perspective view of a typical plant of 'Keiser' grown in an outdoor nursery.

The photograph on the second sheet is a close-up view of typical flowers of 'Keiser'.

DETAILED BOTANICAL DESCRIPTION

The aforementioned photographs and following observations, measurements and values describe plants grown in Grand Haven, Mich. during the summer and autumn in an outdoor nursery and under conditions which closely approximate commercial production. Plants were three years old when the photographs and the description were taken. In the description, color references are made to The Royal Horticultural Society Colour Chart, 1995 Edition, except where general terms of ordinary dictionary significance are used.

Botanical classification: *Abelia chinensis* 'Keiser'.

Parentage:

*Female, or seed, parent.*—Unnamed selection of *Abelia chinensis,* not patented.

*Male, or pollen, parent.*—Unnamed selection of *Abelia chinensis,* not patented.

Propagation:

*Type.*—By softwood cuttings.

*Time to initiate roots.*—About 24 days at 24° C.

*Time to produce a rooted young plant.*—About 90 days at 24° C.

*Root description.*—Fine.

*Rooting habit.*—Freely branching; moderately dense.

Plant description:

*Plant form and growth habit.*—Perennial shrub; upright and outwardly spreading plant habit; inverted triangle; vigorous growth habit.

*Branching habit.*—Freely branching habit, dense and bushy growth habit, lateral branches potentially developing at every node; pinching enhances lateral branch development.

*Plant height.*—About 40 cm.

*Plant diameter* (*area of spread*).—About 64 cm.

Lateral branch description:

*Length.*—About 34 cm.

*Diameter.*—About 2 mm.

*Internode length.*—About 2.5 cm.

*Aspect.*—Upright to outwardly spreading.

*Texture.*—Young, slightly pubescent; older, woody.

*Color.*—Developing: Close to 183A. Fully developed: Close to 198A to 198C.

Foliage description:

*Arrangement.*—Opposite, simple.

*Length.*—About 4 cm.

*Width.*—About 2 cm.

*Shape.*—Ovate.

*Apex.*—Acute to acuminate.

*Base.*—Obtuse.

*Margin.*—Slightly serrate.

*Texture, upper and lower surfaces.*—Smooth, glabrous.

*Venation pattern.*—Pinnate.

*Color.*—Developing leaves, upper surface: Close to 147A tinted with close to 183A. Developing leaves, lower surface: Close to 147B tinted with close to 183A. Fully expanded leaves, upper surface: Close to 137A tinted with close to 183A; midrib, close to 145A, lateral venation, close to 141B. Fully expanded leaves, lower surface: Close to 141A; venation, close to 141A.

*Petiole.*—Length: About 5 mm. Diameter: About 1 mm. Texture, upper and lower surfaces: Smooth, glabrous. Color, upper and lower surfaces: Close to 137A.

Flower description:

*Flower appearance/arrangement.*—Single funnelform flowers arranged on terminal and axillary panicles; freely flowering habit with about 45 flowers per inflorescence.

*Fragrance.*—Fragrant, pleasant.

*Flower longevity.*—Flowers last for about one to two weeks on the plant; flowers not persistent.

*Natural flowering season.*—Plants flower continuously from July to October in Michigan.

*Inflorescence height.*—About 6 cm.

*Inflorescence width.*—About 7 cm.

*Flower diameter.*—About 1.2 cm.

*Flower depth.*—About 2 cm.

*Flower bud.*—Length: About 1 cm. Diameter: About 4 mm. Shape: Obovate. Color: Close to 155D tinted with close to 66C.

*Petals.*—Arrangement/quantity: Single whorl of five fused petals. Lobe length: About 5 mm. Lobe width: About 4 mm. Shape: Roughly spatulate. Apex: Obtuse. Margin: Entire. Texture, upper and lower surfaces: Smooth, glabrous. Color: When opening and fully opened, upper surface: Close to 155D. When opening and fully opened, lower surface: Close to 155D tinted with close to 66D.

*Sepals.*—Quantity/arrangement: Five; three are fused; calyx, star-shaped. Length: About 6 mm. Width: About 3.5 mm. Shape: Elliptic. Apex: Acute. Base: Cuneate. Margin: Entire. Texture, upper and lower surfaces: Smooth, glabrous. Color: Immature, upper surface: Close to 149A overlain with close to 185C. Immature, lower surface: Close to 185C. Mature, upper and lower surfaces: Close to 185C.

*Peduncles.*—Length: About 5 cm. Diameter: About 1.5 mm. Strength: Strong, flexible. Texture: Smooth, glabrous. Angle: Mostly upright. Color: Close to 185A.

*Pedicels.*—Length: About 2 mm. Diameter: About 0.5 mm. Strength: Strong, flexible. Texture: Smooth, glabrous. Angle: Upright to about 10°. Color: Close to 185A.

*Reproductive organs.*—Stamens: Quantity per flower: Four. Anther length: About 1.5 mm. Anther shape: Oblong. Anther color: Close to 66C. Pollen amount: Scarce. Pollen color: Close to 155D. Pistils: Quantity per flower: One. Pistil length: About 2.5 cm. Stigma shape: Globular. Stigma color: Close to 155D. Style length: About 2 cm. Style color: Close to 155D. Ovary color: Close to 137D.

*Seeds/fruits.*—Seed and fruit development have not been observed on plants of the new *Abelia* plant.

Garden performance: Plants of the new *Abelia* have been observed to have excellent garden performance and to tolerate rain, wind and a wide temperature range.

Pathogen/pest resistance: Plants of the new *Abelia* have not been shown to be resistant to pathogens and pests common to *Abelia.*

It is claimed:

1. A new and distinct *Abelia* plant named 'Keiser' as illustrated and described.

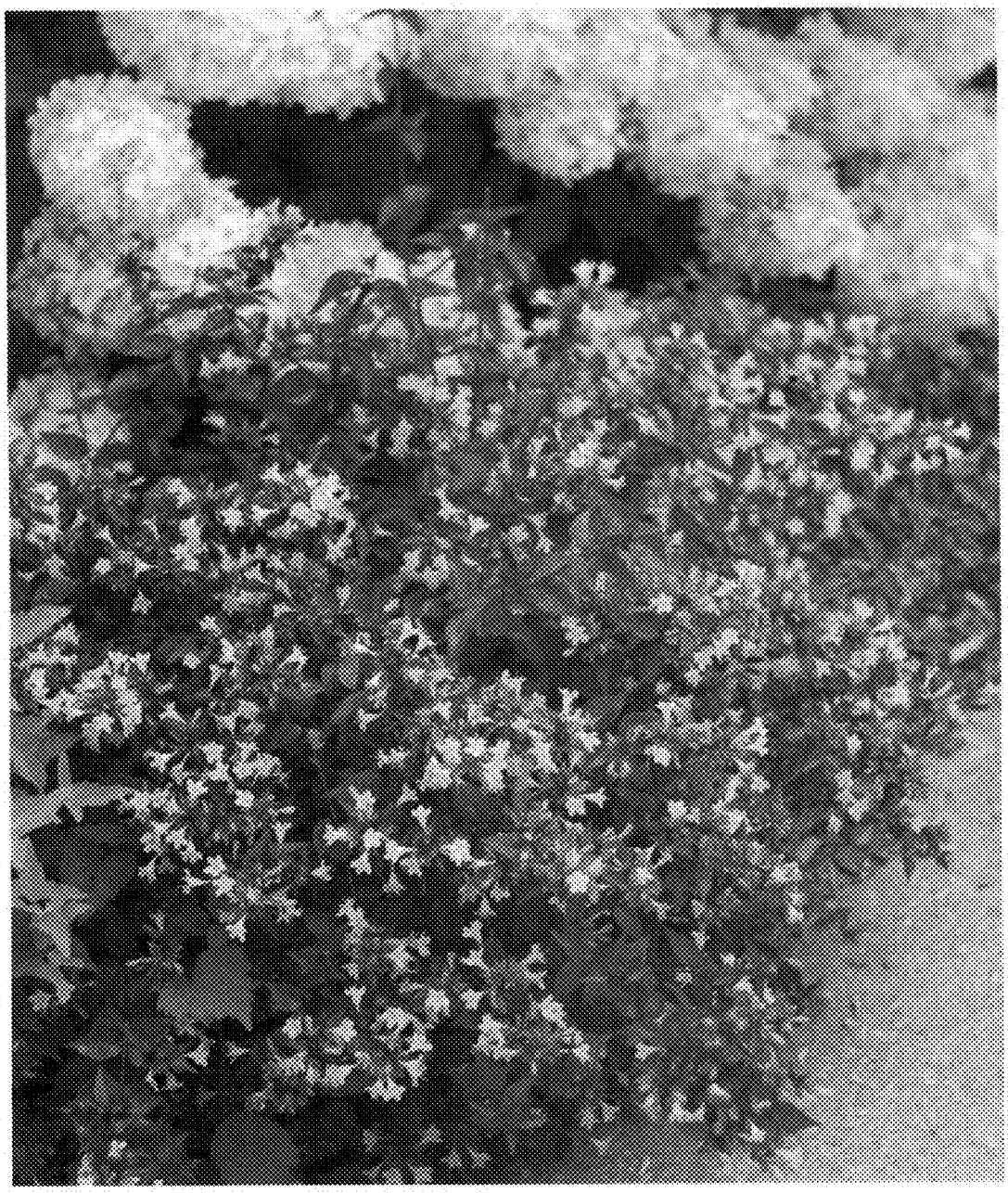

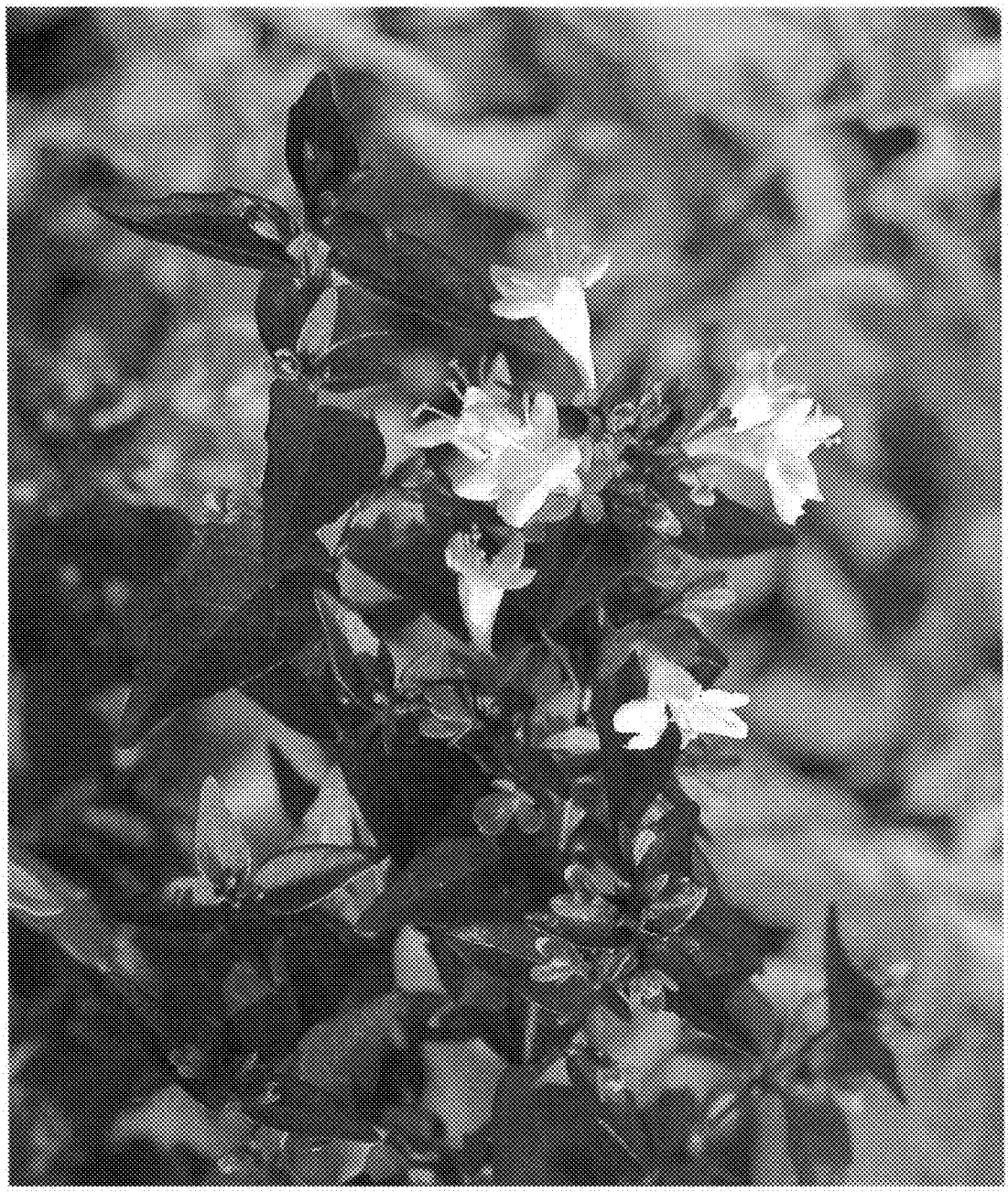

* * * * *